United States Patent
Bos (10) Patent No.: US 7,074,949 B2
(45) Date of Patent: Jul. 11, 2006

(54) ZINC GLYCEROLATE COMPOSITION AND METHOD FOR MANUFACTURE THEREOF

(75) Inventor: Michael Ary Bos, Pearcedale (AU)

(73) Assignees: Micronisers PTY LTD, Victoria (AU); Imperial Chemical Industries PLC, London (GB)

( * ) Notice: Subject to any disclaimer, the term of this patent is extended or adjusted under 35 U.S.C. 154(b) by 0 days.

(21) Appl. No.: 11/042,216

(22) Filed: Jan. 25, 2005

(65) Prior Publication Data

US 2005/0222444 A1    Oct. 6, 2005

Related U.S. Application Data (63) Continuation of application No. PCT/AU03/00943, filed on Jul. 25, 2003.

(30) Foreign Application Priority Data

Jul. 26, 2002  (AU) ............................... 2002950437

(51) Int. Cl.
*C07F 3/06*    (2006.01)
*C08L 61/00*   (2006.01)

(52) U.S. Cl. ..................................... 556/130; 525/515
(58) Field of Classification Search ................ 556/130; 525/515

See application file for complete search history.

(56) References Cited

U.S. PATENT DOCUMENTS 4,544,761 A    10/1985  Taylor et al. ................ 556/130

FOREIGN PATENT DOCUMENTS

| WO | WO87/01379 | 3/1987 |
|---|---|---|
| WO | WO92/09549 | 6/1992 |
| WO | WO95/08524 | 3/1995 |

*Primary Examiner*—Porfirio Nazario-Gonzalez
(74) *Attorney, Agent, or Firm*—Gauthier & Connors LLP (57) ABSTRACT

The invention provides a method for preparing zinc glycerolate comprising reacting a zinc compound with glycerine wherein the zinc compound is selected from the group consisting of hydrozincite and zinc oxide prepared by calcining hydrozincite.

17 Claims, 6 Drawing Sheets

ZINC GLYCEROLATE COMPOSITION AND METHOD FOR MANUFACTURE THEREOF

PRIORITY INFORMATION

This application is a Continuation of International Application No. PCT/AU2003/00943, filed Jul. 25, 2003, which claims priority to Australian Application No. 2002950437, filed Jul. 26, 2002, both of which are incorporated herein by reference in their entirety.

The present invention relates to a zinc glycerolate composition to a method of manufacture of zinc glycerolate and to polymer compositions comprising zinc glycerolate.

BACKGROUND

Zinc glycerolate has been used in pharmaceutical preparations and as an additive used in plastics, rubber and resins to confer special properties.

Blewett et al in U.S. Pat. No. 3,859,236 describes the stabilisation of vinyl halide resin compositions with divalent metal propanetriolates, in particular, the stabilisation of vinylchloride polymers with a zinc compound. The zinc propanetriolate was prepared from zinc acetate and a large excess of glycerol by heating under nitrogen to 160° C. for 6 hours to give a yield of only 34% based on the zinc. Reaction at 220° C. gave quantitative yield. A similar reaction, using zinc carbonate at 200° C., afforded the product in 79% yield.

Taylor in United Kingdom Patent 2,101,132B (U.S. Pat. No. 4,544,761) describes a method for combining a zinc compound with propanetriol to afford a polymeric and plastic plate-like zinc propanetriolate. The method of preparation of this polymer comprised mixing zinc oxide, or a zinc oxide forming material, with propanetriol in the proportion of about fifty parts by weight of zinc-containing compound to approximately 500 parts by weight of propanetriol, raising the temperature to about 260° C. and maintaining that temperature under constant stirring until added zinc oxide was predominantly converted to the propanetriolate, with evolution of water. The reaction was claimed to proceed at lower temperatures more slowly. The zinc propanetriolate polymer had to be isolated from the large excess of glycerol by pouring the cooled mixture into water, filtering, washing and drying. The material has been shown to possess a layered structure by T. J. Hambly and M. R. Snow in Aust. J. Chem 36, 1249 (1983).

Taylor in U.S. Pat. No. 4,876,278 (PCT International Application WO 87/01281; AU86/00251; United Kingdom 2,191,941) describes pharmaceutical applications of zinc propanetriolate. He describes a method of applying the material through transdermal absorption. It is claimed to have fungicidal, antiarthritic, antimicrobial and bacteriostatic activity.

Taylor in Australian patent 584,238 (PCT International Application WO 87/01379; AU86.00249) describes a modification of rubber and plastics by addition of the zinc propanetriolate material prepared in a manner as described above in United Kingdom 2,101,132B during manufacture or processing, as well as controlling the addition and processing to selectively arrange the additive particles in the organic polymer, thereby improving either the tensile strength of the composite material or its resistance to deterioration by ultraviolet light.

In U.S. Pat. No. 4,544,761, Taylor claims that the reaction between ane excess of propanetriol and a zinc compound can occur at temperatures around 260° C. For example, propanetriol (5.4 mole) and zinc oxide (0.614 mole) were reacted together at 260° C. for 1 hour to afford a 90% yield of polymer. The reaction was also stated to be slow below a temperature of 210° C.

In U.S. Pat. No. 4,943,326, Taylor claims that crystalline zinc propanetriolate could be formed by subjecting a zinc oxide suspension in propanetriol to microwave irradiation. Although this technique involved a saving in time, the temperature for effective conversion was subsequently found to exceed 190° C. Again a large excess of glycerol was required.

Bos in U.S. Pat. No. 5,475,123 describes a method of manufacture of zinc glycerolate which involves reacting a divalent metal including zinc, a polyhydroxy compound and a catalyst such as zinc acetate.

Typically the zinc glycerolate of the prior art is made up of crystals of 1 to 100 micrometer and usually from 10 to 1000 micrometer. Pin milling or jet milling may be used to reduce the size to 1 to 20 microns.

When zinc glycerolate of 1 to 20 microns is used as a nucleating agent it is difficult to disperse and deagglomerate causing blocking of extruder screens and resulting in a plastic product of low clarity, high haze and physical properties less then desirable.

SUMMARY

We have now found that formation of zinc glycerolate from hydrozincite (zinc hydroxycarbonates), which exists as species such as $Zn_5(OH)_6(CO_3)_2$, allows production of a very fine zinc glycerolate. The sizes which can be achieved are typically less than 100 nanometres. We have found zinc glycerolate of such sizes to be excellent as a nucleating agent in plastics.

Accordingly we provide a method of preparing zinc glycerolate comprising reacting a zinc compound with glycerine wherein the zinc compound is hydrozincite or is zinc oxide prepared by calcining hydrozincite.

In a particularly preferred aspect of the invention the zinc glycerolate is contacted with a dispersing agent. We have found that the particle size distribution and performance of the product is significantly improved if hydrozincite is reacted with glycerine in the presence of a dispersing agent. The dispersing agent is preferably selected from the group consisting of polymeric dispersants such as poly(12-hydroxystearic acid) and fatty acids and derivatives of fatty acids particularly fatty acid esters such as glycerol esters of fatty acids and fatty amides such as ethylene bis stearamide.

The more preferred dispersants are fatty acid esters formed with polyhydroxy alcohols particularly glycerol. We have found that these dispersants, particularly fatty acid ester dispersants, form a coating to stabilize nano size particles of zinc glycerolate and facilitate their uniform dispersion in polymer compositions or other formulations. Glycerol monostearate is the most preferred dispersant. The dispersant also improves the efficiency of the reaction and the performance of the zinc glycerolate in polymeric compositions by reducing agglomeration and haze.

In a further aspect the invention provides a polymeric composition comprising at least one polymer and a zinc glycerolate composition preferably comprising a dispersant as hereinbefore described.

The particle size of the zinc glycerolate is preferably less than 500 nm, more preferably less than 200 nm, still more preferably less than 150 nm and most preferably is less than 100 nm. Indeed we have found that zinc glycerolate formed by the process of the invention will typically enable particle sizes of 10 to 80 nm to be prepared which are well dispersed.

In a further aspect the invention provides a zinc glycerolate composition comprising particulate zinc glycerolate of number average particle size less than 100 nm and preferably a dispersant bound to the surface thereof.

DETAILED DESCRIPTION

The process of the invention involves forming zinc glycerolate from hydrozincite. We have found that by using hydrozincite the particle size of zinc glycerolate which can be achieved is significantly smaller than can readily be achieved by known methods such as described by Taylor in U.S. Pat. No. 4,789,701.

Hydrozincite has a porous structure and without wishing to be bound by theory we believe that by using hydrozincite to form glycerolate the porous nature of the hydrozincite allows small particles of zinc glycerolate to be prepared without the high intensity milling that would otherwise be necessary.

The zinc glycerolate may, in accordance with the invention, be prepared from hydrozincite using either of two methods. The first method which is less preferred, is to calcine hydrozincite to form zinc oxide and to react the zinc oxide with glycerine preferably in the presence of dispersant. The hydrozincite is preferably calcined at a temperature at which it is converted to zinc oxide. Typically the temperature will be in the range of from 230 to 400° C. although higher temperatures may be used if desired. The temperature will to some extent control the particle size of the zinc oxide which may be readily prepared.

This aspect of the invention will typically include a step of high sheer mixing or milling to reduce the particle size. We have generally found that high sheer mixing is efficient to reduce the particle size to less than 100 nm although milling may be used if desired. An example of a suitable high sheer mixer is the Sigma Z-arm mixer.

In the preferred aspect of the method of the invention hydrozincite is reacted directly with glycerine (without calcination to form zinc oxide as an intermediate). Reaction of hydrozincite with glycerine is preferably conducted in the presence of the dispersant as described above.

Hydrozincite has a porous structure and reaction with glycerine, particularly in the presence of dispersant produces nanometre sized crystals at sites within the structure. The resulting crystals of zinc glycerolate within the porous structure can readily be separated from one another by low energy milling and/or mixing. Indeed we have found that particles produced by this aspect of the invention may be reduced in size to less than 100 nm as a result of processing routinely used in plastic processing. For example, porous hydrozincite particles of 0.2–3 micron may be used to form zinc glycerolate with a crystal size of less than 80 nm and low intensity milling or mixing may be used to provide a particle size of zinc glycerolate which is less than 100 nm and in many cases approximates the size of crystals.

The energy required to reduce the particle size of zinc glycerolate prepared by this method is generally significantly less than would be required to reduce the particle size of glycerolate prepared by conventional methods Milling may be carried out to reduce the particle size of hydrozincite, zinc oxide, zinc glycerolate or at two or more of these stages in preparation. However milling required to reduce particles below crystal size generally needs to be of much higher energy.

The hydrozincite used in the method of the invention is preferably of particle size in the range of from 10 nm to 3000 nm and more preferably 20 nm to 500 nm. Hydrozincite may and preferably will be prepared by reaction of zinc oxide or a water soluble salt of zinc with carbon dioxide or a water soluble carbonate such as ammonium or sodium carbonate. The hydrozincite is preferably prepared by reacting an aqueous slurry of zinc oxide with carbon dioxide gas.

The particle size of the zinc oxide used in preparation of the hydrozincite is not narrowly critical but will typically be 20 nm to 1000 microns, preferably 100 to 300 nm mean particle size. The formation of hydrozincite in this method results in a significant reduction in density thereby producing porous particles and allowing particle size reduction without the expense of high intensity milling.

The zinc compound used in the method of the invention (namely hydrozincite or zinc oxide) is preferably reacted with glycerine in a stoichiometric amount or with a slight excess for example up to 10% of glycerine. The amount of dispersant used in the composition is not narrowly critical but is preferably 1–10% and more preferably 5% by weight.

The reaction with glycerine may be conducted in the presence of a catalyst to minimize the reaction rate or allow lower temperature conditions to be used. Where used the catalyst is preferably an acid or acid salt such as a lower alkyl carboxylic acid (e.g. $C_2$ to $C_6$ carboxylic acid), such as acetic acid, naphthenic acid, benzoic acid, citric acid, oxalic acid, salicylic acid, steric acid, boric acid, trifluoro acidic acid or mixture thereof.

The catalyst may be a salt such as an alkali or alkaline earth metal salt. Preferred salts are the sodium potassium, zinc or calcium or magnesium salt. The weight of catalyst to zinc compound may be in the range of from 1:10000 to 1:5.

The reaction between the particulate zinc compound hydrozincite or zinc oxide and glycerine is preferably carried out at a temperature in the range of from 100° C. to 250° C. more preferably 120 to 180° C. and most preferably 120 to 160° C.

A further aspect of the invention relates to a polymer composition comprising at least one polymer and zinc glycerolate having mean particle size of less than 1000 nm preferably less than 200 nm more preferably less than 100 nm and most preferably 10 to 80 nm. Generally at least 90% of particles are of particle size of less than 100 nm.

The preferred polymers are organic polymers such as selected from organic polymers and polymer blends chosen from the following types, polyethylene, polypropylene, polyvinyl chloride, polystyrene, polyacrylamide, polyester, polyamide or poly(acrylonitrile-butadiene-styrene). A polyolefin such as polypropylene is preferred. These polymers may then be processed into polymeric articles such as fibres, films, fabrics or coatings.

The zinc glycerolate material may be present in amounts of from approximately 0.01 to 20% by weight based on the total weight of the polymeric blend. In the final plastics product the concentration is generally in the range of 0.01 to 2% but master batch composition for preparation of the product may contain up to 20% by weight. The organic polymer may be present in amounts of approximately 80% to 99.99% by weight based on the total weight of the polymeric blend.

Accordingly, in a preferred aspect there is provided a polymeric composition including approximately 80 to 99.9% by weight based on the total weight of the polymeric composition of an organic polymer; and approximately 0.01 to 2% by weight based on the total weight of a zinc glycerolate having a particle size such that at least 80% of the particles are of approximately 100 nm or less.

Zinc glycerolate remains unchanged when incorporated into the polymer during processing (see Australian Patent 584,238) for characteristic XRD powder pattern but if used in topical medical applications it may hydrolyse in aqueous environment.

The polymeric composition may further include conventional compounding ingredients in minor amounts. Compounding ingredients such as pigments, fillers, extenders, flame retardants, antioxidants, mould release agents, acid scavengers and the like may be incorporated into the polymeric composition.

We have found that zinc glycerolate prepared according to the present invention provides high clarity and higher improved crystallization temperatures. Improvements are particularly evident for propylene homopolymer and copolymers and polypropylene blends.

Most nucleating agents with higher crystallization temperatures such as sodium benzoate, lithium benzoate and aluminium para tertiary butyl benzoate can not be mixed with benzylidene sorbitols to give improved clarity with high crystallization temperatures.

We have found that zinc glycerolate can be mixed with benzylidene sorbitols to improve crystallization temperatures (and other physical properties), preferably we have found that by mixing the (Prifer 3888) with benzylidene sorbitol (Irgaclear DM or millad 3988) in a ratio of 10:1 to 1:10 preferably 1:1, we achieve high clarity combined with improved crystallization temperatures and hence improved physical properties when compared to polypropylene with only benzylidene sorbitols such as Irgaclear DM or Millad 3988.

The zinc glycerolate prepared by the method of the invention may be used in topical medicaments. Zinc glycerolate is known for use as a topical antifungal and antiviral agent and for treatment of prevention of foot odour. The composition of the invention comprising smaller particle sizes then has heretofore been described provides more effective transdermal absorption enabling less effective agent to achieve the same topical effect as the prior art. The composition of the invention also has the benefit of allowing more efficient dispersion particularly in oil bases which may be used for topical application.

The invention will now be described with reference to the following examples. It is to be understood that the examples are provided by way of illustration of the invention and that they are in no way limiting to the scope of the invention.

EXAMPLE

Methods

Except where otherwise specified the reference in this specification to particle size refers to the number mean particle size as determined by laser light analysis such as used in Example 7.

Aspects of examples of the invention are discussed in Examples 5 to 7 with reference to the attached drawings.

IN THE DRAWINGS:

FIG. 5 shows the XRD results from the hydrozincite prepared according to Example 1a.

The reaction of glycerol, nano size particles of hydrozincite and surfactant (with or without acetic acid) may be conducted in a wide variety of reactors, provided that there is good mixing of the components. The reaction may be performed in a mixer of the Z-arm type, sigma mixer, capable of being heated. The temperature of the reaction should be 120–160° C.

Example 1

(a) Preparation of Hydrozincite

Zinc oxide is mixed with water in a vertical stainless steel reactor with a high speed dispersion blade, carbon dioxide is fed into a sparge ring below the mixer and a shower of $CO_2$ bubbles are introduced to the mix, where they react with the zinc oxide to form hydrozincite, when the reaction is complete, metal level 58.0–59.0%, the product is filtered to provide a wet cake.

This wet cake can be calcined to produce nano zinc oxide or reacted directly with glycerine to produce nano zinc glycerolate.

Note 1: When the zinc oxide is reacted with carbon dioxide, an option is to use a NETZCH top mill and introduce the $CO_2$ into the stirred bead cage. This will provide high shear mixing during reaction and will provide smaller hydrozincite porous particles. Which when calcined to form zinc oxide would provide smaller porous zinc oxide particles.

(b) Preparation of Zinc Glycerolate from Hydrozincite

Nano size zinc hydrozincite (1692 gm) glycerol (428 gm), wetting agent Solsperse 21000 (38 gm) and Glycerol Monostearate (9 gm), Acetic acid as a Catalyst (3.6 gm) were mixed together in a 2 L Z-arm mixer capable of being heated. The slurry was heated to 120–130° C. and kept at that temperature for 4–5 hours. The final white powder obtained exhibited an XRD pattern characterizing zinc glycerolate.

Example 2

The experiment in Example 1b was repeated on 1/10 scale but with the omission of the acetic acid catalyst and wetting agent Solsperse 21000 and increased level of Glycerol Monostearate.

Nano size hydrozincite (16000 gm), glycerol (4438 gm) and Glycerol Monostearate (413 gm) were mixed together in a 30 L Z-arm mixer capable of being heated. The slurry was heated to 100° C. and kept at that temperature for 6 hours during which time the reaction went to completion. At the end of the experiment the temperature was raised up to 130°

C. to make sure that all moisture was eliminated. The moisture level at the end of the reaction was 0.2%. The XRD testing performed on the finished product showed that it was zinc glycerolate.

Example 3

The experiment in Example 2 was repeated on the same scale but with the omission of Gycerol Monostearate and in the presence of acetic acid. Nano size hydrozincite (16000 gm), glycerol (4045 gm) and acetic acid (34 gm) were mixed together in a 30 L Z-arm mixer capable of being heated. The slurry was heated to 120° C. and kept at that temperature for 8 hours during which time the reaction went to completion. The XRD testing performed on the finished product showed that it was zinc glycerolate.

Example 4

Manufacturing Procedure for Nano Particle Zinc Glycerolate.

| Equipment |  |
|---|---|
| Stainless steel jacketed 300 L sigma mixer with hot oil heating | |
| Load | |
| Glycerin | 53.5 Kg @ 98.56% |
| Wet hydrozincite cake prepared from 50 Kg of Zinc Oxide and prepared according to Example 1(a) | |
| Glycerol mono stearate (Smoothex 60 LFG) | 5.0 Kg |

Glycerin (53.5 Kg) was loaded into the sigma mixer and the amount of wet hydrozincite, equivalent to 50.0 Kg of zinc oxide was added slowly with mixing. The glycerol monostearate was added and the composition mixed to a thin paste. The composition was then heated to 160° C. and held at 160° C. for 16 hours and the water vapour removed to provide a dry flowable powder of the following specification.

| Check: | |
|---|---|
| Moisture | below 0.5% |
| Metal level | 38–42% zinc |
| Particle size | 20–70 nm |
| Form | Free flowable powder |
| Colour | white |

| Quality control results: | |
|---|---|
| Moisture | 0.3% |
| Metal level | 40.34% |
| Particle size | 51.6 nm |
| Yield | 93.0 Kg |

Example 5

Methods

Zinc glycerolate prepared according to Example 1 was coated onto the popypropylene pellets as dry powders at 0.1 wt % using a Hobart mixer. The coated pellets of ST 611 random copolymer were then extruded through a Theysohn co-rotating twin screw extruder. Coated pellets of random copolymer RFR6100H were compounded with a melt temperatures of 149–164° C. and 9–16 bar pressure. Similarly, coated pellets of XS6500H homopolymer were compounded with a melt temperature of 170–190° C. and 4–10 bar pressure. Samples were extruded as continuous rod, which was cooled to ambient temperature prior to pelletization.

Figure 1:
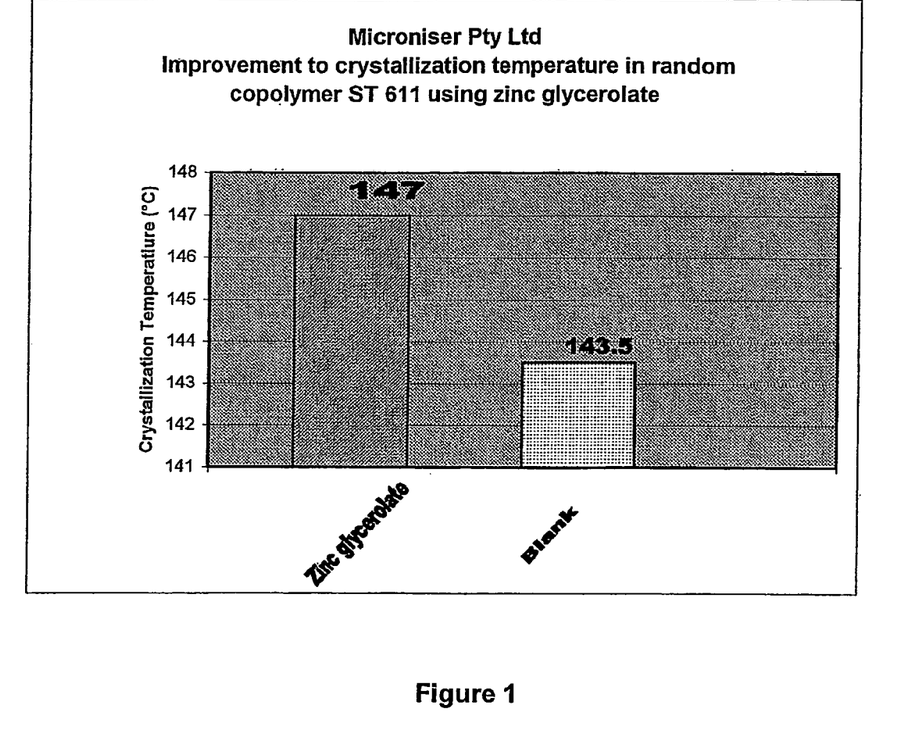
FIG. 1 is a graph comparing the crystallisation temperature of a polypropylene copolymer containing added zinc glycerolate prepared (see in Example 5) with the corresponding blank without zinc glycerolate.
Figure 2:
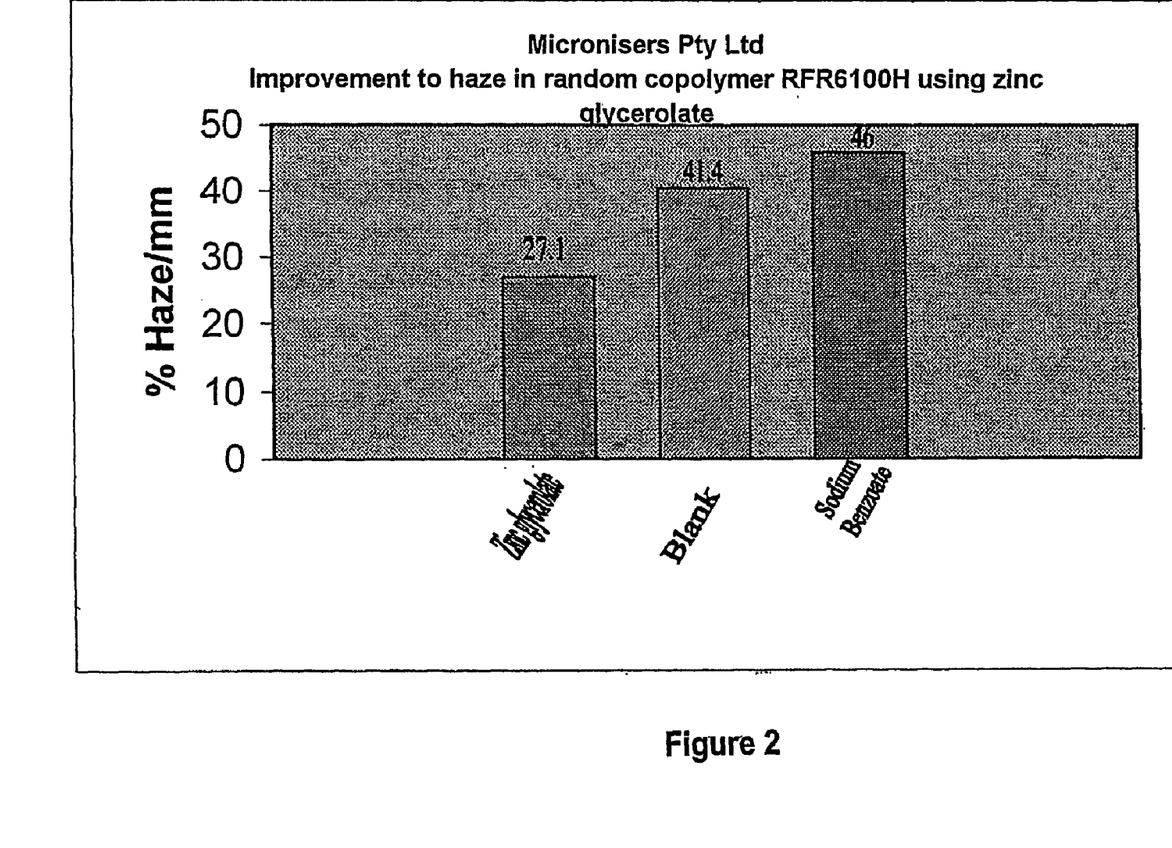
FIG. 2 is a graph comparing the haze of a random copolymer RFR6100H containing added zinc glycerolate (see Example 5) with the corresponding blank without zinc glycerolate and a comparative composition containing sodium benzoate nucleating agent.
Figure 3:
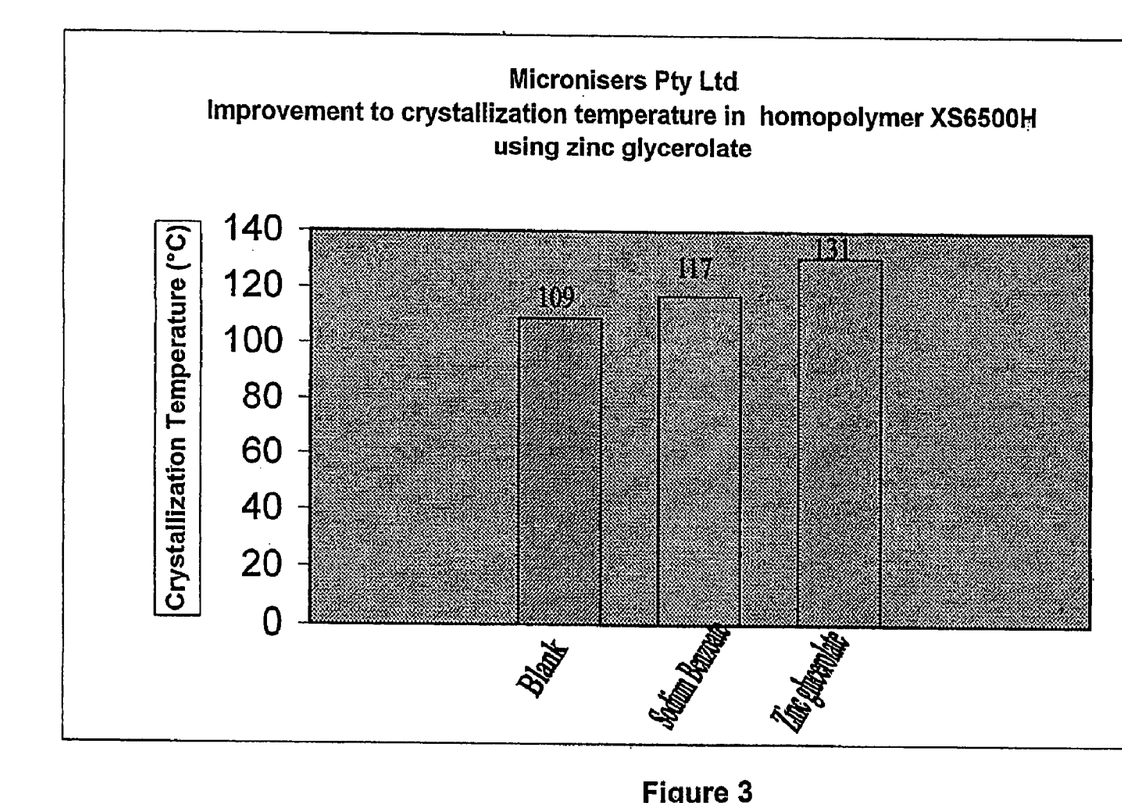
FIG. 3 is a graph comparing the crystallization temperature of XS6500H homopolymer containing added zinc glycerolate with the corresponding blank (without zinc glycerolate) and a comparative example containing sodium benzoate nucleating agent.

The effect of zinc glycerolate on crystallization temperature of random copolymer ST 611 is shown in FIG. 1, the effect of zinc glycerolate on haze in random copolymer RFR6100H is shown in FIG. 2. The effect of zinc glycerolate on crystallization temperature of XS6500H homopolymer is shown in FIG. 3.

Example 6

Figure 4:
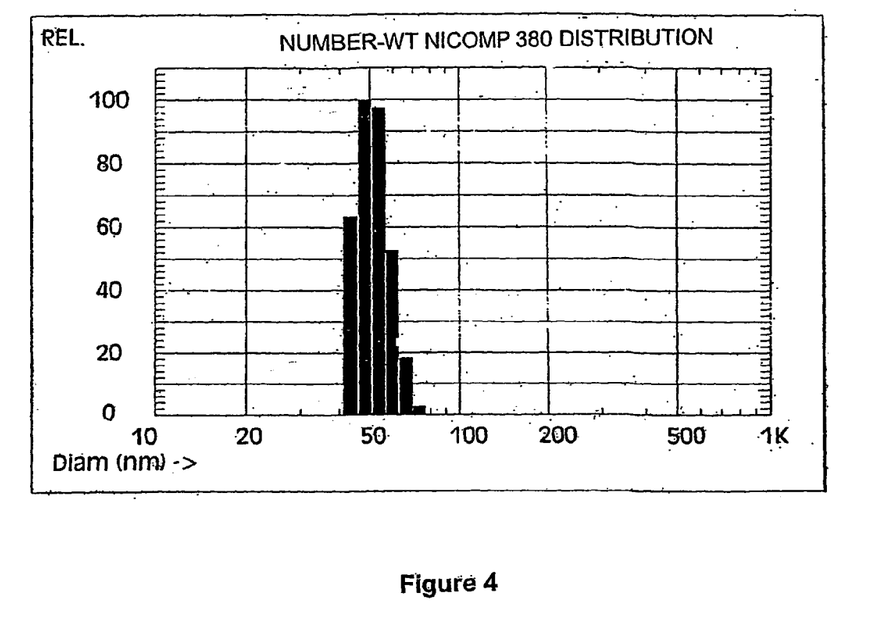
FIG. 4 is a graph showing the size analysis (by laser light) of zinc glycerolate prepared according to Example 4.

Zinc glycerolate prepared according to the method of Example 4 was subject to laser light size analysis to measure the number mean average particle size. The results are shown in the graph below and determined that the number mean diameter was 51.6 nm.

Number—Weighted NICOMP DISTRIBUTION Analysis (Solid Particle)

| NICOMP SUMMARY: | |
|---|---|
| Peak #1: Mean Diameter = 50.6 nm, S. Deviation = 6.4 nm (12.6%), Number = 100.0% | |
| SN4511.1 | |
| Mean Diameter = 51.6 nm   Fit Error = 7.430   Residual = 98.807 | |
| NICOMP SCALE PARAMETERS: | |
| Min. Diameter = 10 nm | Plot Size = 45 |
| Smoothing = 3 | Plot Range = 100 |
| GAUSSIAN SUMMARY: | |
| Mean Diameter = 20.7 nm | Chi Squared = 36.521 |
| Stnd. Deviation = 286.6 nm (138.1%) | Baseline Adj. = 0.000% |
| Coeff. of Var'n = 1.381 | Mean Diff. Coeff. = 6.90E−009 $cm_2$/s |
| Run Time = 0 Hr 30 Min 45 sec | Wavelength = 632.8 nm |
| Count Rate = 24 KHz | Temperature = 20° C. |
| Channel #1 = 786.8K | Viscosity = 30.000 cp |
| Channel Width = 130.0 uSec | Index of Ref. = 1.447 |

Example 7

Figure 5:
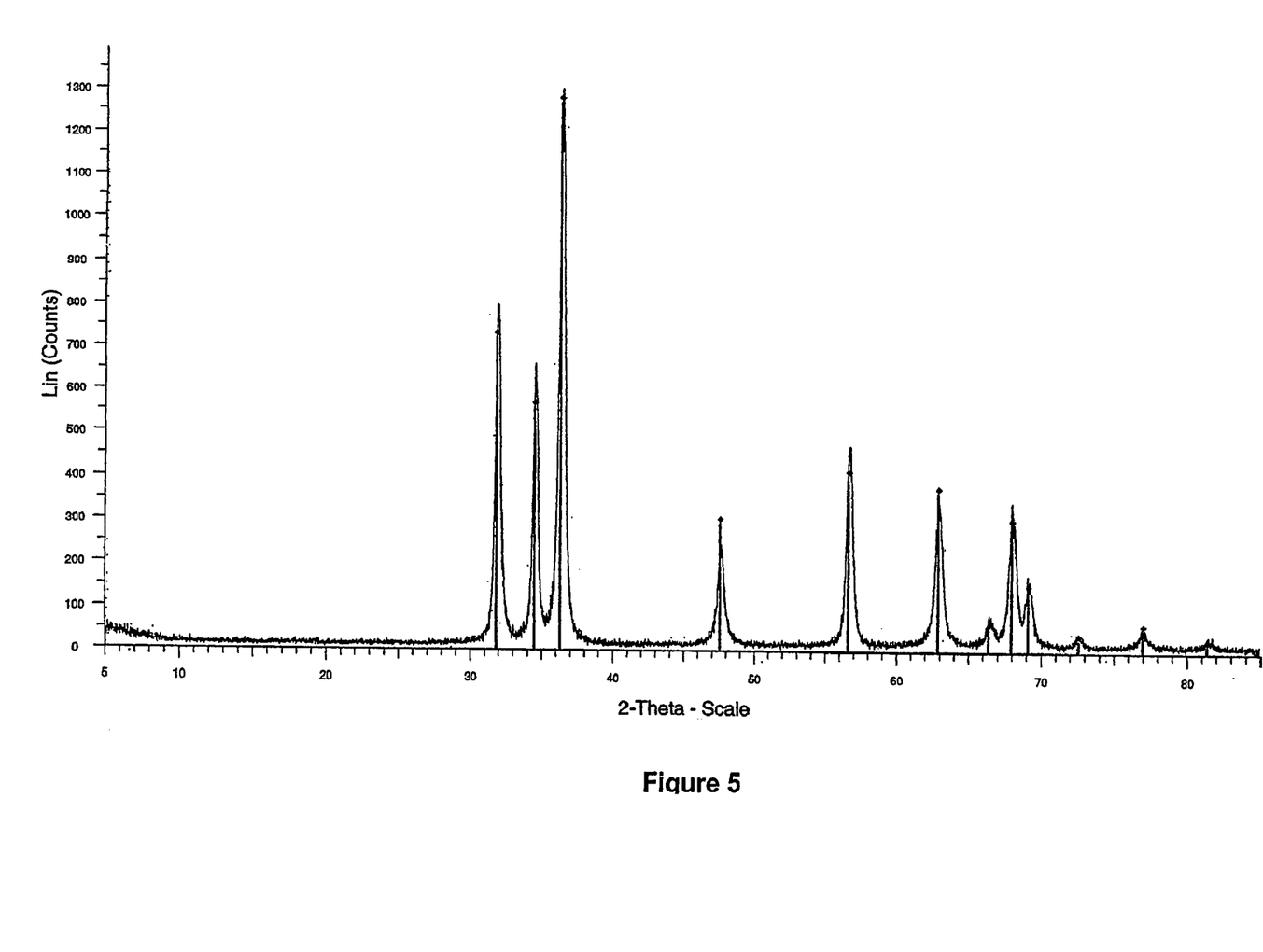
Figure 6:
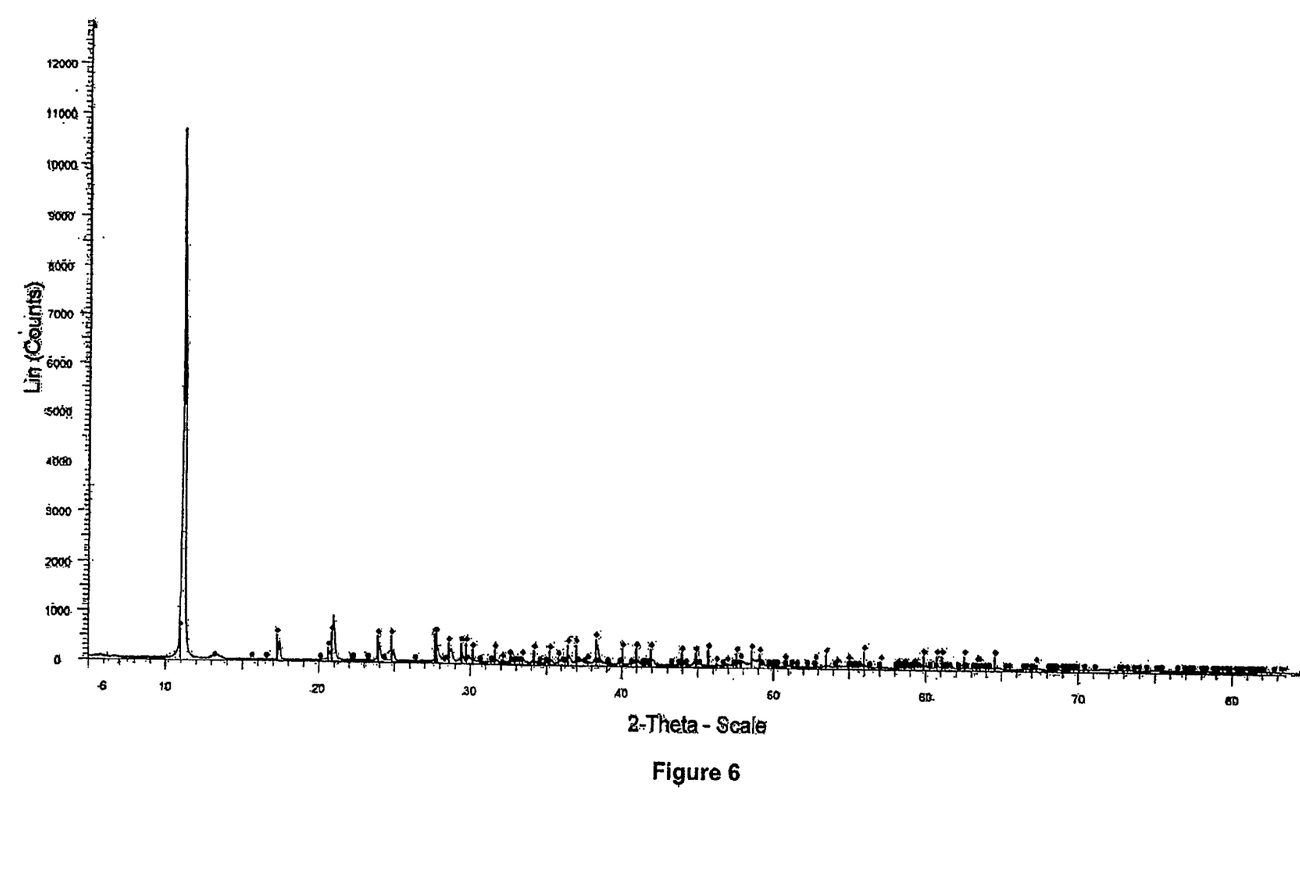
FIG. 6 shows the XRD results from the zinc glycerolate prepared according to Example 4.

XRD and Rietveld analysis was carried out on the hydrozincite prepared according to Example 1a and the zinc glycerolate of Example 4. The XRD results on hydrozincite and Prifer 3888 are shown in FIGS. 5 and 6 respectively. The Rietveld results on hydrozincite and Prifer 3888 are shown below.

| DATA DESCRIPTION | | |
|---|---|---|
| Phase Number | Mineral Name | Phase Name |
| 1 | Hydrozincite | Zinc Carbonate Hydroxide |
| 2 | Zinc Glycerolate | Zinc (II) Monoglycerolate |

QUANTITATIVE RESULTS

| Phase Number | Conc. [Wt %] | error [Wt %] |
|---|---|---|
| 1 | 1.3 | 0.2 |
| 2 | 98.7 | 1.4 |

CRYSTAL SIZE/STRAIN

| Phase Number | Size [Å] | error [Å] | Strain (rms) | Error (rms) |
|---|---|---|---|---|
| 1 | 263 | 38 | 0.0000 | 0.0000 |
| 2 | 545 | 8 | 0.4791 | 0.0115 |

UNIT CELL

| Phase No. | a [Å] | b [Å] | c [Å] | alpha [°] | beta [°] | gamma [°] | |
|---|---|---|---|---|---|---|---|
| 1 | 13.54241 | 6.36657 | 5.31498 | 90.0000 | 94.7724 | 90.0000 | |
|   | 0.00976 | 0.01790 | 0.01922 | 0.0000 | 0.1512 | 0.0000 | Error |
| 2 | 8.10409 | 6.39490 | 8.68661 | 90.0000 | 93.4437 | 90.0000 | |
|   | 0.00204 | 0.00189 | 0.00255 | 0.0000 | 0.0200 | 0.0000 | Error |

ATOMIC DISPLACEMENT PARAMETERS

| Phase Number | B [Å$^2$] | error [Å$^2$] |
|---|---|---|
| 1 | −2.8689 | 0.7473 |
| 2 | 9.8519 | 0.1423 |

ZERO POINT

| −0.0615 [°2theta] | Error 0.0031 [°2theta] |
|---|---|

The zinc glycerolate was found to have a crystallite size of 54.5 nm and the hydrozincite a crystallite size of 26.3 nm.

The correlation between crystallite size of Example 7 and the particle size determined in Example 6 shows that the particles of zinc glycerolate are well Odispersed and finely divided to approximate the size of individual crystals. In cases where agglomeration is evident we would expect a particle size (ie size of agglomerate to be significantly larger than the crystallite size).

The invention claimed is:

1. A method for preparing zinc glycerolate comprising reacting a zinc compound with glycerine wherein the zinc compound is selected from the group consisting of hydrozincite and zinc oxide prepared by calcining hydrozincite.

2. A method according to claim 1 wherein the zinc glycerolate has a particle size less than 100 microns.

3. A method according to claim 1 wherein the particle size of zinc glycerolate is in the range of from 20 to 80 nm.

4. A method according to claim 1 wherein the zinc compound is reacted with glycerine in the presence of a dispersing agent.

5. A method according to claim 4 wherein the dispersing agent is selected from the group consisting of polymeric dispersants, fatty acids and fatty acid esters.

6. A method according to claim 4 wherein the dispersant is selected from poly(12-hydroxy stearic acid) and fatty acid glycerol esters.

7. A method according to claim 4 wherein the dispersant is present in an amount of from 1 to 10% by weight of the reaction mixture.

8. A method according to claim 1 wherein hydrozincite is reacted with glycerine.

9. A method according to claim 8 wherein the reaction is carried out at a temperature of from 100 to 250° C.

10. A method according to claim 8 wherein the reaction is carried out at a temperature in the range of from 120 to 180° C.

11. A method according to claim 1 comprising subjecting the zinc glycerolate to low energy mixing to reduce the particle size to less than 100 nm.

12. A method according to claim 1 wherein the hydrozincite is prepared by reaction of zinc selected from zinc oxide and water soluble salts of zinc with carbon dioxide or a water soluble carbonate.

13. A method according to claim 12 wherein the hydrozincite is prepared by reacting an aqueous slurry of zinc oxide with carbon dioxide.

14. A method according to claim 13 wherein the mean particle size of the zinc oxide is in the range of from 100 to 300 nm.

15. A polymeric composition comprising an organic polymer; from 0.01 to 20% by weight of the total composition of zinc glycerolate; benzylidene sorbitol; and wherein at least 80% of particles of zinc glycerolate have a size no more than 100 nm.

16. A polymeric composition according to claim 15 wherein the organic polymer is selected from at least one of polyethylene, polypropylene, polyvinyl chloride, polystyrene, polyacrylamide, polyester, polyamide or poly(acrylonitrile-butadiene-styrene).

17. A polymeric composition according to claim 15 wherein the ratio of zinc glycerolate to benzylidene sorbitol is in the range of from 10:1 to 1:10.

* * * * *